United States Patent [19]

Allington

[11] 4,140,396
[45] * Feb. 20, 1979

[54] MEASURING INSTRUMENT

[75] Inventor: Robert W. Allington, Lincoln, Nebr.

[73] Assignee: Instrumentation Specialties Company, Lincoln, Nebr.

[*] Notice: The portion of the term of this patent subsequent to Jul. 6, 1993, has been disclaimed.

[21] Appl. No.: 836,053

[22] Filed: Sep. 23, 1977

Related U.S. Application Data

[60] Division of Ser. No. 699,877, Jun. 25, 1976, Pat. No. 4,073,492, which is a continuation-in-part of Ser. No. 251,712, May 9, 1972, Pat. No. 3,967,492.

[51] Int. Cl.² .......................................... G01N 21/46
[52] U.S. Cl. .................................. 356/361; 73/190 R
[58] Field of Search ................... 73/27, 190 R, 61.1 C; 23/230, 253 R; 356/107

[56] References Cited

U.S. PATENT DOCUMENTS

| 2,650,496 | 9/1953 | Middleton et al. | 73/204 |
| 2,782,102 | 2/1957 | Howe | 73/27 X |
| 3,967,492 | 7/1976 | Allington | 73/190 R |
| 3,992,940 | 11/1976 | Platzer | 73/204 |

Primary Examiner—Herbert Goldstein
Attorney, Agent, or Firm—Vincent L. Carney

[57] ABSTRACT

To reduce errors in a measuring instrument caused by temperature effects from changes in the flow rate of fluids passing through the instrument, the flow of heat is adjusted to balance the flow-rate-dependent temperature increases against the flow-rate-dependent temperature decreases that occur with the same change in flow rate in each flow path. Some of the techniques for adjusting the flow of heat are: (1) controlling the temperature of the fluid at the inlet of the instrument with one heat exchanger and the temperature of the body of the instrument with another heat exchanger; (2) controlling the temperature of the walls of the instrument with a heating coil; and (3) emitting heat within the flow path from a transducer.

18 Claims, 9 Drawing Figures

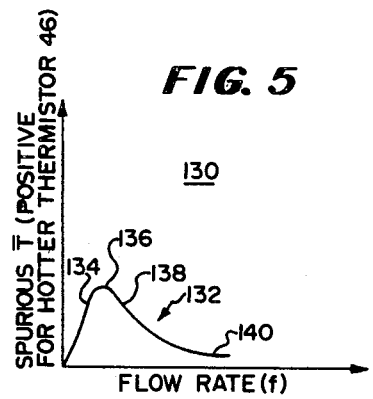
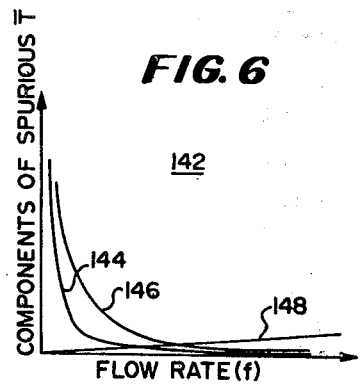
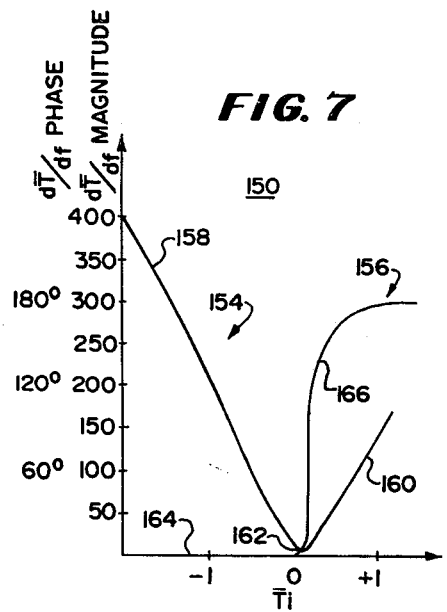
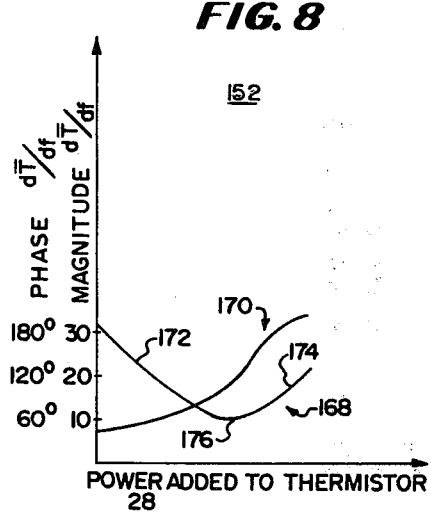

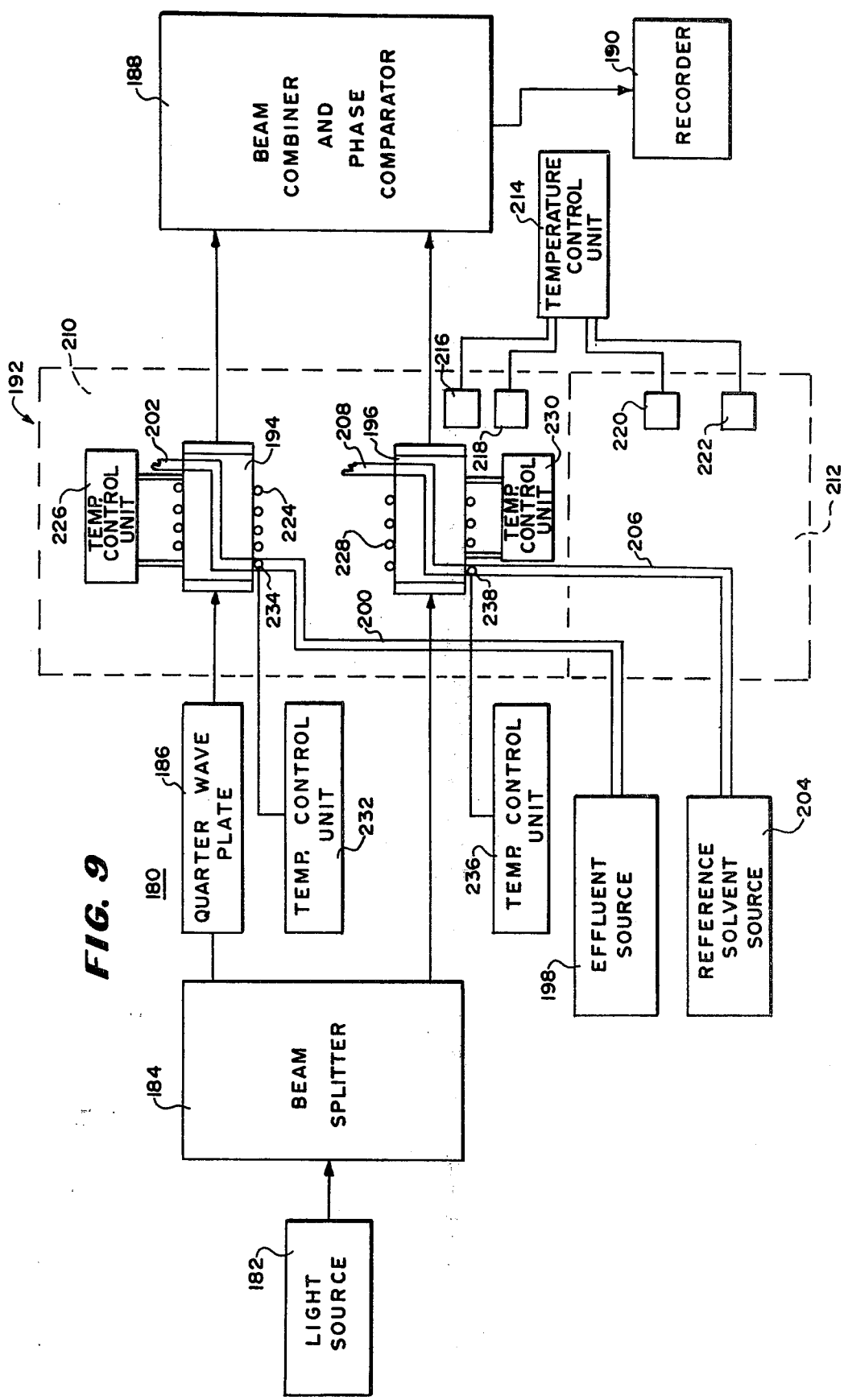

MEASURING INSTRUMENT

This is a division of application Ser. No. 699,877 filed June 25, 1976 now U.S. Pat. No. 4,073,492, which was a continuation-in-part of U.S. patent application Ser. No. 251,712 filed May 9, 1972 now U.S. Pat. No. 3,967,492.

This application is a continuation-in-part of U.S. patent application Ser. No. 251,712 filed May 9, 1972, for Heat of Interaction Detector by Mr. Robert W. Allington.

This invention relates to measuring instruments and more particularly relates to apparatuses and methods for reducing errors from temperature effects caused by changes in the flow rates of fluids passing through the instruments.

In one class of measuring instrument, one or more passageways receive a fluid or fluids, and measure some characteristic of the fluid generally to determine the nature of substances carried by the fluid. The rate of flow of the fluid in the passageway or passageways are subject to variations from the pumping sources and these variations may cause errors in the measurements. It has been found that one cause of such errors results from temperature effects within the fluid.

One type of measuring instrument in which it has been known that temperature effects cause errors due to flow rate changes is a heat of interaction detector. One type of heat of interaction detector, for example, includes a passageway through which a fluid passes, an interactive material within the passageway that interacts with an ingredient of the fluid to absorb or release heat, and a temperature measuring device in the vicinity of the interactive material to measure the changes in temperature caused by the heat that is released or absorbed. A second temperature measuring device is positioned to assume the temperature of the fluid and serves as a reference, with the difference between the two temperature measuring devices indicating the temperature difference that is caused by the release or absorption of heat. An arrangement is also included in some heat of interaction detectors of this type to reduce flow-rate-dependent temperature errors in the temperature measurement, which errors result from changes in the temperatures that occur with changes in the flow rate of the fluid passing through the heat of interaction detector.

In some prior art heat of interaction detectors of this type, the arrangement for reducing the flow-rate-dependent temperature errors includes wall portions of the passageway in the vicinity of the two temperature measuring devices, which wall portions are of material having high thermal conductivity and which form a restricted diameter passageway for the fluid. This arrangement is intended to remove heat from the fluid as it passes between the two temperature measuring devices in such a quantity as to compensate for the flow-rate-dependent temperature increases between the two temperature measuring devices. An arrangement of this type is described in U.S. Pat. No. 3,535,918 to Munk and in a corresponding article by Munk and Raval entitled "Flow Sensitivity of the Micro Adsorption Detector," published in the Journal of Chromatographic Science, Vol. 7, Jan. 1969, pp. 49–55.

The prior art arrangement for reducing the flow-rate-dependent temperature errors has the disadvantages of not producing reliable results and of being difficult to adapt to different carrier fluids, flow rates, and temperature conditions. The results of the prior art arrangement are unreliable in that the prior art arrangement reduces the flow-rate-dependent temperature errors by different amounts in an unpredictable manner under what appear to be the same conditions. The prior art arrangement is difficult to adapt to different carrier fluids, flow rates and temperature conditions because it is not easily adjustable, requiring in some cases the insertion of a different wall portion to provide a different thermal transfer characteristic for such adjustment.

Other prior art heat of interaction detectors include apparatus by which the heat transfer characteristics of the wall portions are more easily adjusted. For example, a calorimeter is disclosed in U.S. Pat. No. 3,467,501 to Groszek having a heating coil around a temperature shield in which the calorimeter is mounted to maintain the temperature shield at a constant temperature when the calorimeter is operated at an elevated temperature. However, this type of prior art heat of interaction detector does not include apparatus specifically intended to compensate for flow-rate-dependent temperature errors nor apparatus for automatically controlling the heating element.

Accordingly, it is an object of the invention to provide a novel apparatus and method for reducing the flow-rate-dependent temperature errors in instruments.

It is a still further object of the invention to provide an apparatus and a method for balancing flow-rate-dependent temperature increases against the flow-rate-dependent temperature decreases that occur with the same change in flow rates in instruments that measure characteristics of fluids.

It is a still further object of the invention to provide an apparatus and a method for easily adjusting an instrument for measuring a characteristic of a fluid to reduce the flow-rate-dependent errors caused by temperature effects.

It is a still further object of the invention to provide an instrument that can be adjusted to reduce the flow-rate-dependent errors that are caused by temperature effects without being disassembled and while remaining in operation.

It is a still further object of the invention to provide an apparatus and a method for controlling the flow of heat within an instrument for measuring a characteristic of a fluid.

It is a still further object of the invention to provide an instrument for measuring a characteristic of fluids that is insensitive to fluctuations in ambient temperature and inlet stream temperature.

It is a still further object of the invention to provide a method and apparatus for reducing the flow-rate-dependent error caused by temperature effects of an instrument for measuring a characteristic of a fluid to a minimum by adjusting one or more of the heat flow paths in the instrument.

It is a still further object of the invention to provide a method and apparatus for reducing the flow-rate-dependent error caused by temperature effects of an instrument to a minimum by adjusting the difference between the temperature of a fluid entering the inlet of the instrument and the temperature of the body of the instrument.

It is a still further object of the invention to provide a method and apparatus for reducing the flow-rate-dependent temperature error of an instrument for measuring a characteristic of a fluid to a minimum by adjusting the temperature of the walls of the instrument.

It is a still further object of the invention to provide a method and apparatus for reducing the flow-rate-dependent temperature error of an instrument for measuring a characteristic of a fluid by adjusting the heat emitted by heating devices within the instrument for measuring a characteristic of a fluid, which heating devices may be the temperature measuring devices in heat of interaction detectors.

It is a still further object of the invention to provide a method and apparatus for reducing the flow-rate-dependent error of an instrument for measuring a characteristic of a fluid by adjusting the average temperature of the fluid in the instrument.

In copending patent application Ser. No. 251,712, a heat of interaction detector is disclosed having an adjustable heat-flow control means. Before operating the heat of interaction detector to measure the heat of interaction of the active ingredient in the fluid and the interactive material, the flow-rate-dependent temperature error of the heat of interaction detector is detected and reduced to a minimum by adjusting the heat-flow control means.

The heat-flow control means is adjusted while the flow rate is varied until the rate of change of the difference in the temperatures of the reference temperature measuring device and the heat of interaction measuring device is a minimum. At this point, the heat flow factors that cause flow-rate-dependent temperature increases are balanced against the factors that cause flow-rate-dependent temperature decreases with the same magnitude of change in the flow rate of the fluid.

It has been discovered that a similar procedure reduces errors in certain other instruments which do not measure temperature directly and, indeed, in instruments which compare measurements of two different flow streams, one being a reference flow stream and the other being a flow stream containing a substance a characteristic of which is to be measured. Even though the temperature is not directly measured in these instruments, errors are introduced in the measurement by fluctuations in temperature, which fluctuations are flow-rate-dependent. Such errors are not removed by the comparison with measurements in the flow stream under some circumstances.

In one embodiment, the heat-flow control means includes two heat excahngers for each flow stream, one of which controls the temperature of the inlet fluid to the instrument and the other of which controls the temperature of the body of the instrument. The temperature of the fluid entering the instrument is adjusted with respect to the temperature of the body of the instrument until a minimum flow-rate-dependent temperature error results.

When applied to a heat of interaction detector, there is a single flow stream and two heat exchangers which in cooperation with each other control the temperature of the fluid entering the detector with respect to the temperature of the body of the detector. When applied to other instruments such as a refractometer, there are two flow streams, with heat exchangers to control the temperature of the fluid entering the instrument with respect to the body of the instrument. In the case of a refractometer, the errors in refractive index of the fluids are flow-rate-dependent because of temperature changes caused by variations of the flow rate in the two streams with respect to each other and these errors are reduced to a minimum by the temperature control system.

In another embodiment of the instrument, the temperatures of the fluids at the inlets of the two flow streams of a refractometer are individually controlled by heaters adjusted to the flow streams or actually in the flow streams. This embodiment enables each flow stream to be individually adjusted.

In still another embodiment, the heat-flow control means includes one or more heating coils which impart an adjustable amount of heat to the walls of the instrument to control their temperature. The temperature of the walls of the instrument is adjusted until the minimum flow-rate-dependent error results.

In still another embodiment which measures temperature directly, the temperature measuring devices are thermistors and the heat-flow control means is a circuit for controlling the heat emitted by the thermistors. With this arrangement, the temperature in the vicinity of one of the thermistors is adjusted with respect to the temperature in the vicinity of the other thermistor until a minimum flow-rate-dependent temperature error results.

With these structures and methods of operation, the instrument of this invention has several advantages over the prior art instruments for measuring a characteristic of a fluid such as: (1) it provides consistent and reproducible reductions in the flow-rate-dependent errors; (2) it is less sensitive to fluctuations in the ambient temperature and inlet stream temperature; and (3) it may be easily adjusted without disassembling and without terminating its operation.

The above-noted and other features of the invention will be better understood from the following detailed description when considered with reference to the accompanying drawings in which:

FIG. 5 is a graph illustrating the relationship between the flow-rate-dependent temperature error and the flow rate of the carrier fluid for a typical heat of adsorption detector;

FIG. 6 is a graph illustrating the relationship between the components of the flow-rate-dependent temperature error shown in FIG. 5 and the flow rate of the carrier fluid for a typical heat of adsorption detector;

FIG. 7 is a graph showing the experimentally-determined relationship between the rate of change of the flow-rate-dependent temperature error with respect to changes in the rate of flow of the carrier and the difference between the inlet temperature of the carrier fluid and the temperature of the body of a heat of adsorption detector or a refractometer;

FIG. 8 is a graph showing the experimentally-determined relationship between the rate of change of the flow-rate-dependent temperature with respect to changes in the rate of flow of the carrier and the power added to thermistors in the embodiment of FIG. 2; and FIG. 9 is a block diagram of a refractometer in accordance with the invention.

STRUCTURE OF FIRST EMBODIMENT

Figure 1:
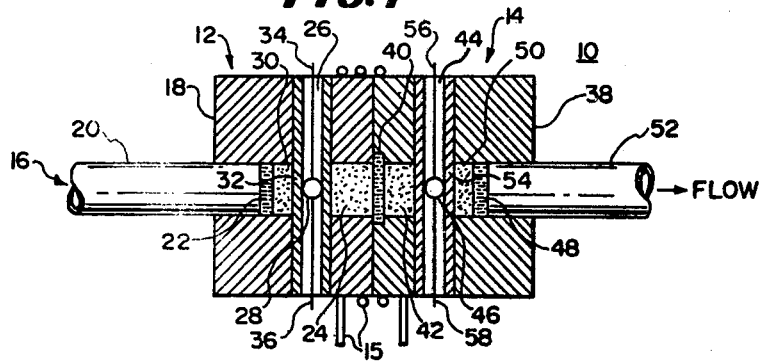
FIG. 1 is a simplified longitudinal sectional view of a portion of a heat of adsorption detector including an embodiment of the invention.

In FIG. 1, there is shown, in a longitudianl sectional view, a basic portion of a heat of interaction detector 10 having an inlet section 12 and an outlet section 14 positioned contiguous with each other and clamped together by any suitable clamping means (not shown), with a central fluid passageway 16 passing through both sections 12 and 14. A heat flow control means, which in one embodiment is a heating coil 15, is wound around the outer walls of the central portions of the inlet section 12 and the outlet section 14.

The heat of interaction detector 10 may be considered as a calorimeter or instrument for measuring the heat transferred as a result of the contact between a fluid passing through the fluid passageway 16 and a solid or semisolid that is relatively stationary within the heat of interaction detector 10 and includes instruments for measuring any of the different heats of interaction, such as the heats of sorption, adsorption, absorption, preferential sorption, chemical reaction and the like. Moreover, it may be used for other related purposes such as to: (1) determine the surface area of powders which release heat in proportion to their surface areas when they are contacted by certain fluids or (2) detect a specific chemical by incorporating an enzyme that is specific to the chemical as part of the solid or semisolid, in which case the heat of the enzyme-catalyzed reaction provides a measure of the amount of the specific chemical in the fluid. However, although the principles of the invention have more general application, a heat of adsorption detector will be specifically described hereinafter as the preferred embodiment for the purposes of explanation.

The inlet section 12 includes an inlet support body 18, a cylindrical inlet tube 20, an inlet porous separating disc 22, an inert packing material 24, a transverse, cylindrical, sleeved, reference-temperature hole 26, a reference-temperature measuring device 28, which is a thermistor in the preferred embodiment, and a cylindrical inlet support hole 30.

To provide a path for the fluid to flow past the reference-temperature measuring device 28, the cylindrical inlet support hole 30 passes through the inlet support body 18 from an inlet end to an inner end, where it communicates with the outlet section 14. The inlet porous separating disc 22 is mounted near the center of the cylindrical inlet support hole 30, having a tight fit against the internal walls thereof, with the cylindrical inlet tube 20 extending along the inlet support hole 30 from one side of the inlet porous separating disc 22 through the inlet end of the support body 18 to receive the fluid and with the inert packing material 24 being located in the support hole 30 between the other side of the inlet porous separating disc 22 and the inner end of the inlet support body 18 adjacent to the outlet section 14.

To provide a reference measurement of temperature, the transverse, cylindrical reference-temperature hole 26 extends through a central portion of the inlet support body 18 in a direction perpendicular to the cylindrical inlet support hole 30, intersecting the cylindrical inlet support hole 30 near the center of the inlet support body 18. A reference-temperature tube 32, having a smaller diameter than the cylindrical inlet support hole 30, fits tightly within the reference-temperature hole 26 and contacts the inert packing material 24, which otherwise extends throughout the cylindrical inlet support hole 30 between the inlet porous separating disc 22 and the central end of the inlet support body 18. The thermistor 28 is mounted within and contacts the walls of the reference-temperature tube 32 near the center of the cylindrical inlet support hole 30, with one conductive lead wire 34 extending in one direction and the other conductive lead wire 36 extending in the opposite direction along the transverse, cylindrical reference-temperature hole 26 out of diametrically opposite wall portions of the inlet support body 18.

The outlet section 14 includes an outlet support body 38, a central porous separating disc 40, an interacting medium 42, a transverse, cylindrical, sleeved, temperature-measuring hole 44, a temperature-measuring device 46, which is a thermistor in the preferred embodiment, an outlet porous separating disc 48, a cylindrical outlet support hole 50, and a cylindrical outlet tube 52.

To provide a path for the fluid to flow past the temperature-measuring device 46, the cylindrical outlet support hole 50 passes through the outlet support body 38 from an inner end, where it communicates with the cylindrical inlet support hole 30 to an outlet end. At the inner end, the cylindrical outlet support hole 50 includes a counterbore into which the central porous separating disc 40 is fitted. The outlet porous separating disc 48 is mounted near the center of the cylindrical outlet supporting hole 50, having a tight fit against the internal walls thereof, with the cylindrical outlet tube 52 extending along the outlet support hole 50 from one side of the outlet porous separating disc 48 through the outlet end of the support body 38 to release the fluid and with the interacting medium 42 being located in the support hole 50 between the other side of the outlet porous disc 48 and the central porous disc 40 adjacent to the inlet section 12.

To provide for the measurement of temperature, the outlet transverse, cylindrical temperature-measuring hole 44 extends through a center portion of the outlet support body 38 in a direction perpendicular to the cylindrical outlet support hole 50, intersecting the cylindrical outlet support hole 50 near the center of the outlet support body 38. A temperature-measuring tube 54, having a smaller diameter than the cylindrical outlet support hole 50, fits tightly within the temperature-measuring hole 44 and contacts the interacting medium 42, which otherwise extends throughout the cylindrical outlet support hole 50 between the central porous separating disc 40 and the outlet porous separating disc 48. The thermistor 46 is mounted within and contacts the walls of the temperature-measurement tube 54 near the center of the cylindrical outlet support hole 50, with one conductive lead wire 56 extending in one direction and the other conductive lead wire 58 extending in the opposite direction through the transverse, cylindrical temperature-measuring hole 44 and out of diametrically opposite wall portions of the outlet support body 38.

The specific materials used for the inert packing material 24, the porous discs 22, 40, and 48 and the interactive material 42 are selected for their effect or lack of effect with the active ingredient in the fluid that is forced through the central passageway 16 in a manner known in the art. The interactive material may be, for example, activated silica gel or aluminum oxide to detect the heat of adsorption of organic compounds in the fluid for the purpose of identifying organic compounds in an organic solution from the heat of adsorption given off by the contact between the compounds and the interactive material. The inert packing material may be smooth glass beads, because little heat of adsorption is provided by adsorption of most organic compounds on smooth glass beads. Since every material has a definite heat of adsorption with every other material, there are, of course, many alternative materials which may be used for the interactive material and the inert materials in the embodiment that is a heat of adsorption detector and still further materials in other embodiments using the principles of this invention.

OPERATION OF FIRST EMBODIMENT

One use of the heat of adsorption detector 10 is to detect different separated zones of different organic compounds within a fractionated liquid or gas mixture from the time of occurrence of their heats of adsorption and desorption as they pass through the central fluid passageway 16 and to actuate a fraction collector to collect each or certain of the zones into different containers as described in U.S. Pat. No. 3,151,639 to Robert W. Allington. Another use of the heat of adsorption detector 10 is to determine the quantity of organic compounds from the magnitude of the detected heats of adsorption and desorption. For example, it may be used to identify, locate and determine the quantity of the different eluates in a carrier solvent after elution chromatography to aid in the collecting of the eluates.

Before using the heat of adsorption detector 10 for either of these purposes, an interacting material 42 is selected, which interacting material must release substantial amounts of heats of adsorption when contacted by the eluates that are to be detected. The interacting material 42 is assembled with the rest of the parts of the detector as shown in FIG. 1 and described above.

In the operation of the heat of adsorption detector 10 the heat flow control means 15 is first adjusted to reduce the sensitivity of the heat of adsorption detector 10 to changes in the rate of flow of the carrier liquid and then the carrier liquid and eluates are caused to flow through the fluid passageway 16 to generate signals as each eluate is adsorbed and desorbed on and from the interacting material, which signals identify, locate, and determine the quantity of the different eluates or types of eluates in carrier so as to permit their collection by fraction collectors or determinations of their quantities by the amplitudes of the waveforms generated by the heat of adsorption detector 10.

To adjust the heat flow control means 15, pure carrier fluid without eluates is passed through the central fluid passageway 16. As the carrier flows through the heat of adsorption detector 10, the electrical current conducted through the heater coil 15, which is the heat flow control means in the embodiment of FIG. 1, is adjusted to change the amount of heat flowing through the walls of the heat of interaction detector 10 and thus change the temperature of the carrier fluid between the thermistors 28 and 46. While the temperature of the carrier fluid is being adjusted, the rate of flow of the fluid is varied cyclically and the electrical potentials from the thermistors 28 and 46 are compared in a conventional thermistor bridge circuit (not shown in FIG. 1) and observed at each adjustment of the heater current to determine the magnitude of the variation of the output potential from the thermistors as the rate of flow of the carrier liquid changes. A setting of the heat flow control means 15 is found by this procedure for which the difference in potential between the outputs of the two thermistors 28 and 46 is relatively constant as the rate of flow of the fluid changes and this setting maintained.

After the heat flow control means 15 has been properly adjusted to reduce the sensitivity of the heat of adsorption detector 10 to changes in the flow rate of fluid passing through the central fluid passageway 16, the carrier and eluates in the chromatograph column are passed through the central fluid passageway 16 and the difference between the temperatures of the two thermistors 28 and 46 is measured to locate the fluid stream or to identify the eluates.

As the carrier fluid passes through the central fluid passageway 16, it carries eluates that have been separated into zones one by one through the inlet section 12 and the outlet section 14.

To generate a reference potential, the fluid in the inlet section passes through the cylindrical inlet tube 20, the cylindrical inlet porous separating disc 22, and the inert packing material 24 of the inlet section 12. As the eluates pass through the inert packing material 24, they do not release any substantial heat of adsorption so that the inert packing material 24 assumes substantially the temperature of the carrier fluid. Because the reference-temperature tube 32 is relatively small and has a relatively high heat conductivity, it assumes the temperature of the inert packing material which is substantially the same temperature as the carrier fluid so that the reference thermistor 28 provides a relatively constant amplitude output signal serving as a reference that indicates the temperature of the carrier fluid and eluates.

To generate an electrical waveform indicating the beginning of an eluate in the liquid carrier, the liquid carrier in the outlet section 14 passes through the central porous separating disc 40, the interacting medium 42, the outlet porous separating disc 48 and the cylindrical outlet tube 52.

As each eluate flows through the interacting medium, four processes take place, each generating a different portion of a two-part (positive and negative) waveform that locates the beginning and identifies the nature of the eluate in the carrier fluid.

Firstly, as the eluate flows into the interacting medium 42, the interacting medium adsorbs it, releasing the heat of adsorption to raise the temperature of the interacting medium, the temperature-measuring tube 54 and the thermistor 46, which provides an increasing amplitude output signal difference between the thermistors 28 and 46 corresponding to the heat of adsorption of the eluate on the interacting medium 42. This increasing amplitude output signal indicates the beginning location of the eluate and is the leading edge of the positive part of the waveform that indicates the eluate.

Secondly, after the eluate has reached equilibrium on the interacting medium 42, the interacting medium stops adsorbing the eluate, resulting in no further release of heat and in a temperature of the interacting medium 42, the temperature measuring tube 54 and the thermistor 46 that is reduced by the flow of new liquid carrier so as to provide a falling potential difference between thermistors 28 and 46. This falling potential is the trailing edge of positive part waveform which indicates the eluate.

Thirdly, when the eluate has passed the interacting medium, the interacting medium 42 desorbs the eluate into the relatively pure liquid carrier that separates different eluates so as to remove heat from the interacting medium, reducing the temperature of the interacting medium, the temperature measuring tube 54 and the thermistor 46 and resulting in a potential difference between the thermistors 28 and 46 that increases in the opposite direction (thermistor 46 being cooler). This potential difference indicates that the eluate has passed the outlet section 14 and is the leading edge of the negative part of the waveform that indicates the eluate.

Fourthly, after the eluate has been desorbed, the temperature of the interacting medium, the temperature measuring tube 54 and the thermistor 46 is increased to the temperature of the carrier fluid by the carrier fluid resulting in a decreasing potential difference between the thermistors 28 and 46, which is the trailing edge of the negative part of the waveform that indicates the eluate.

The next eluate zone to flow into the heat of adsorption detector 10 causes these four processes to repeat, but the time duration and the amplitude of the signals generated by the thermistor 46 may be different because the heat of adsorption of the new eluate or the width and concentration of the new zone may be different from the previous eluate and zone. The new waveform has a leading edge indicating the location of the beginning of the next eluate in the chromatographic column and other characteristics indicating the quantity of the eluate.

Accordingly, a plurality of waveforms are generated by the heat of absorption detector, each indicating the location of a different eluate and the quantity of the eluate which waveforms may be used to control a fraction collector and to help determine the quantity of the eluates.

As the carrier and eluates flow through the heat of adsorption detector 10, there are some temperature changes between the reference thermistor 28 and the measuring thermistor 46 that are not due to the adsorption or desorption of the eluates but arise from other unintentional causes, some of the other unintentional causes being related to the rate of flow of the carrier through the heat of adsorption detector. For example heat is conducted through the walls of the heat of adsorption detector at a rate that is partly dependent on the flow rate of the liquid carrying the heat. Also, heat generated by the thermistor 28 and by viscous friction between the carrier and the material in the central fluid passageway 16 is carried from upstream to the downstream thermistor 46 at a rate dependent upon the rate of flow of the carrier.

Some of these unintentional, flow-rate-related causes of temperature differences between the thermistors 28 and 46 increase the temperature difference in a first direction and some increase the temperature difference in a second direction, opposite to the first direction as the flow rate changes in any one direction.

The adjustment of the heat flow control means 15 that was performed at the start of the operation of the heat of adsorption detector 10 balances the unintentional flow-rate related causes that increase in the first direction against those that increase in the second direction as the flow rate changes so that the temperature remains relatively stable as the flow rate varies.

STRUCTURE OF SECOND EMBODIMENT

Figure 2:
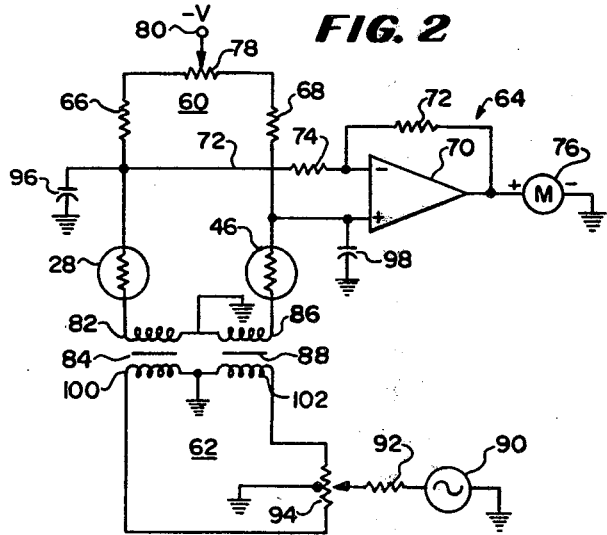
FIG. 2 is a schematic circuit diagram of another portion of a heat of adsorption detector including another embodiment of the invention.

In FIG. 2, there is shown, in a schematic circuit diagram, a bridge circuit 60 useful in indicating the difference between the potential of the thermistors 28 and 46 of the heat of adsorption detector 10 (FIG. 1), with precision. The circuit of FIG. 2 also includes another embodiment of heat flow control means 62 which may be used in place of or together with the heater 15 shown in the embodiment of FIG. 1.

To compare the resistances of the thermistors 28 and 46, the bridge circuit 60 includes: (1) an output circuit 64; (2) two inactive arms, each including a different one of the two resistors 66 and 68; and (3) two active arms, each including a different one of the two themistors 28 and 46, with each of the resistors 66 and 68 and the thermistors 28 and 46 having a different first lead wire and a different second lead wire.

To provide an output potential indicating the difference in the temperatures of the two thermistors 28 and 46, the output circuit 64 of the bridge circuit 60 includes a differential amplifier 70, a feedback resistor 72 connected between the output terminal and the inverting input terminal of the differential amplifier 70, an input resistor 74 connected at one end to the inverting input terminal of the differential amplifier 70 and at its other end to the first lead wire of the resistor 66 and to the first lead wire of the thermistor 28, and a meter 76 connected between the output terminal of the differential amplifier 70 and ground, the positive input terminal of the differential amplifier being connected to the first lead wire of the resistor 68 and to the first lead wire thermistor 46.

The differential amplifier 70 is a high gain operational amplifier that compares the potentials across the thermistors 28 and 46 and provides an output potential that indicates the relative difference in temperature between the thermistors, with the resistors 72 and 74 stabilizing the gain of the amplifier 70.

To supply power to the bridge circuit 60 and to balance it, a variable resistor 78 has one end connected to the second lead wire of the resistor 66 and the other end connected to the second lead wire of the resistor 68, with a source of negative potential 80 being electrically connected to the adjustable tap of the potentiometer. To complete the bridge circuit 60, the second lead wire of the thermistor 28 is connected to one end of a secondary winding 82 of a transformer 84 and the second lead wire of the thermistor 46 is connected to one end of a secondary winding 86 of a transformer 88, with the other ends of the secondary windings 82 and 86 of the transformers 84 and 88 being connected together and to ground. The tap on the variable resistor 78 is adjusted to balance the bridge.

The transformers 84 and 88 are part of the heat flow control means 62, which will be described hereinafter and their secondary windings 82 and 86 have low resistance so that they do not materially affect the operation of the bridge circuit 60. While a meter 76 is connected to the output of the differential amplifier 70 in the embodiment of FIG. 2, other types of indicating and recording instruments may be included instead and the output may also activate a fraction collector to collect zones of the chromatographic column into different containers.

To control the flow of heat within the heat of adsorption detector 10 (FIG. 1), the heat flow control means 62 (FIG. 2) includes an alternating current generator 90, a resistor 92, a potentiometer 94, the transformers 84 and 88, and two capacitors 96 and 98. The transformer 84 includes a primary winding 100 having a first and electrically connected to one end of the potentiometer 94 and the transformer includes a primary winding 102 having a first end connected to the other end of the potentiometer 94, with the second ends of the primary windings 100 and 102 being electrically connected together and to ground.

To permit the flow of power to be directed more to one transformer than the other of the transformers 84 and 88, the adjustable tap of the potentiometer 94 is electrically connected to the generator of alternating current 90 through resistor 92. To provide an alternating current return from the bridge circuit 60, the capacitor 96 has one plate connected to the first lead wires of the resistor 66 and the thermistor 28 and its other plate grounded and the capacitor 98 has one plate connected to the first lead wires of the resistor 68 and the thermistor 46 and its other plate grounded.

OPERATION OF SECOND EMBODIMENT

In the operation of the bridge circuit of FIG. 2, the variable resistor 78 is adjusted with a pure carrier liquid flowing through the central fluid passageway 16 (FIG. 1) of the heat of adsorption detector 10 until the meter 76 is nulled. When the chromatographic carrier solvent flows through the central passageway 16, the meter remains nulled until an eluate reaches the interacting medium 42.

When the eluate reaches the interacting medium 42, it is adsorbed thereon and increases the temperature of the thermistor 46, thereby reducing its resistance. As the resistance of the thermistor 46 falls, a positive going potential is applied to the positive input terminal of the differential amplifier 70 (FIG. 2) by the bridge circuit 60. This positive going potential is amplified by the differential amplifier 70 and applied to the meter 76, which provides a positive deflection.

After equilibrium between the fluid and the interacting medium 42 is reached so that no more eluate is adsorbed, no further heat is released and the temperature of the thermistor 46 falls approximately to solvent temperature so that the output potential from the differential amplifier falls to provide a negative-going potential, returning the meter to its zero deflection.

When the eluate has passed the interacting medium 42 and relatively pure solvent is flowing through the interacting medium 42, the interacting medium desorbs the eluate, removing heat from the temperature measuring tube and the thermistor 46. This causes a further negative-going potential to be applied to the positive terminal of the differential amplifier 70, resulting in the negative deflection of the meter 76. After the eluate has been desorbed, the temperature of the interacting medium 42 returns to the temperature of the solvent, returning the meter to its zero deflection condition.

To control the flow of heat within the heat of adsorption detector 10, alternating current flows from the alternating current generator 90 and the resistor 92 of the heat flow control means 62 through two paths, which are: (1) through a portion of the resistance in the potentiometer 94 and the primary winding 102 of the transformer 88 in series in the order named with a return through ground in the primary circuit of the transformer 88; or (2) through a portion of the resistance in the potentiometer 94 and the primary winding 100 of the transformer 84 in series in the order named, with a return through ground in the primary circuit of the transformer 84. The current through the primary winding 102 of the transformer 88 induces an alternating current potential in the secondary winding 86 of the transformer 88 which causes current to flow through and heat the thermistor 46 and current through the primary winding 100 of the transformer 84 induces an alternating current potential in the secondary winding 82 of the transformer 82 which causes current to flow through and heat the thermistor 28 without affecting the d.c.-responding output circuit 64. There is a return to ground for these currents through the capacitors 96 and 98.

To adjust the flow of heat within the heat of adsorption detector 10, the amount of the heat generated by each of the thermistors 28 and 46 is adjusted by adjusting the potentiometer 94 to increase the resistance in one of the paths and decrease it in the other path of the alternating current power from the alternating current generator 90, thus adjusting the difference between the currents through the two thermistors 28 and 46. The direction and the amount of the flow of heat is adjusted by shifting the relative amounts of heat generated by these currents and released by the two thermistors 28 and 46.

To control the heat flow so as to reduce the sensitivity of the heat of absorption detector to the rate of flow of the carrier, the heat flow control means 62 is adjusted with pure carrier flowing through the heat of adsorption detector 10 in much the same manner as the heat flow control means 15 shown in FIG. 1 is adjusted. To make this adjustment, the rate of flow of the pure carrier is varied at each of several selected adjustments of the potentiometer 94, until an adjustment of the potentiometer 94 results in a minimum amount of deflection of the meter 76 as the rate of flow of the carrier is varied. This embodiment can also be physically realized by placing separate electrically adjustable heating elements adjacent to the thermistors instead of using the thermistors themselves as heating elements.

STRUCTURE OF THIRD EMBODIMENT

Figure 3:
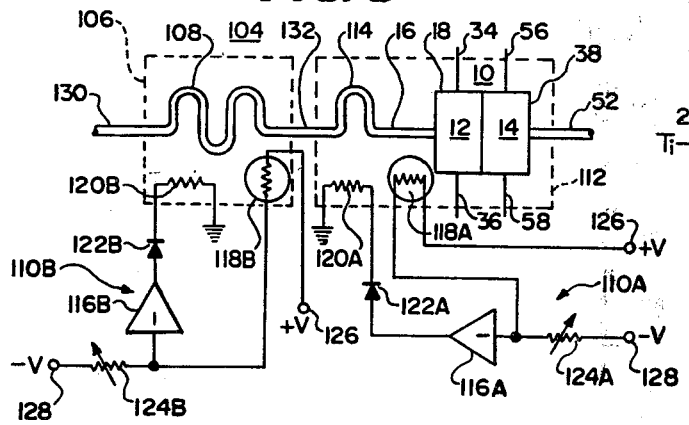
FIG. 3 is a schematic diagram of another embodiment of the invention.

In FIG. 3 there is shown another embodiment of the invention having a heat flow control means 104 connected to the heat of adsorption detector 10. The heat flow control means 104 may be used by itself or with either or both of the heat flow control means 15 and 62 shown in FIGS. 1 and 2.

The heat flow control means 104 includes a first enclosure 106, a first heat exchanger 108, a first temperature control apparatus 110B, a second enclosure 112, a second heat exchanger 114 and a second temperature control apparatus 110A.

The second enclosure 112 preferably includes in its interior a material that has a high degree of thermal conductivity such as water or solid metal so as to provide a uniform temperature throughout. Both enclosures 106 and 112 have insulative casings and are fabricated in any manner known in the art for easy assembly consistent with the general purpose of controlling the temperature of apparatus within their interiors.

The temperature control apparatuses 110A and 110B each include a corresponding one of two inverting amplifiers 116A and 116B, two thermistors 118A and 118B, two resistance heaters 120A and 120B, two diodes 122A and 122B and two potentiometers 124A and 124B. In each of these apparatuses, a source of positive potential 126 is electrically connected to two corresponding parallel circuits through a corresponding one of the thermistors 118, which two parallel circuits include corresponding ones of: (1) the potentiometers 124 and a source of negative potential 128 in series in the order named; and (2) the amplifiers 116, the anodes of the diodes 122, the cathodes of the diodes 122, the resistance heaters 120 and ground in series in the order named.

The heat of adsorption detector 10, the second heat exchanger 114, the thermistor 118A and the resistance heater 120A are within the second enclosure 112 and maintained at the same temperature thereby; the first heat exchanger 108, the thermistor 118B and the resistance heater 120B are in the first enclosure 106 and maintained at the same temperature thereby.

The purpose of the first and second heat exchangers 108 and 114 is to impart a predetermined temperature to the fluid flowing from the chromatograph column before it enters the heat of adsorption detector 10 with respect to the body of the heat of adsorption detector. In the preferred embodiment, the first heat exchanger 108 is relatively long compared to the second heat exchanger 114 and the first enclosure 106 is warmer than the second enclosure 112 with the result that the fluid assumes the temperature of the first enclosure 106 before entering the second heat exchanger 114, which reduces the temperature some before it enters the heat of adsorption detector but not to the temperature within the second enclosure 112 so that it has a different temperature than that of the body of the heat of adsorption detector 10. However, other arrangements can be used to create a predetermined temperature difference between the fluid and the body of the heat of adsorption detector 10, and, indeed, the second heat exchanger 114 could even be dispensed with under some circumstances.

To conduct the carrier fluid through the first and second heat exchangers 108 and 114 and the heat of adsorption detector 10, an inlet conduit 130 communicates at one end with the outlet of the chromatograph column and at its other end with the heat exchanger 108 and a connecting conduit 132 communicates at one end with the first heat exchanger 108 and at its other end with the second heat exchanger 114, the second heat exchanger 114 communicating with the heat of adsorption detector 10 through the inlet tube 20.

OPERATION OF THIRD EMBODIMENT

In the operation of the heat flow control means 104, the heat of adsorption detector 10 operates normally once the heat flow control means 104 has been adjusted for minimum change in the temperature response to the thermistors 28 and 46 (FIGS. 1 and 2) when the rate of flow of the carrier fluid is changed.

While the heat of adsorption detector 10 is operating, the temperatures of the enclosures 112 and 106 are maintained constant at the same or at different temperatures by the temperature control circuits 110A and 110B and the temperatures of the heat of adsorption detector 10 and the second heat exchanger 114 are maintained the same by the heat transfer medium within the enclosure 112. With this arrangement, the heat-flow control means 104 can be adjusted to render the output waveform from the heat of adsorption detector substantially independent of changes of the rate of flow of the carrier fluid within the normal range of changes caused by the pump for the carrier fluid. This is basically done by adjusting the difference between the temperature of the carrier fluid as it enters the heat of adsorption detector 10 and the temperature of the body of the heat of adsorption detector.

The temperature control circuits 110A and 110B operate in the same manner to maintain the temperature of their respective enclosures constant and the operation of only one 110A of the temperature control circuits 110A and 110B will be described herein.

If the temperature within the enclosure 112 changes from the set temperature, the thermistor 118A senses the change and applies a signal to the amplifier 116A which adjusts the current flow through the resistance heater 120A to compensate for the change. If the temperature within the enclosure 112 is reduced below the set temperature, the resistance of the thermistor 118A is increased, resulting in a negative change in the potential at the input of the inverting amplifier 116A. The increase in the negative potential at the input of the inverting amplifier 116A results in an increased positive potential being applied to the resistance heater 120A through the diode 122A, thus supplying more heat to the enclosure 112. Similarly, an increase in the temperature above the set temperature within the enclosure 112 causes a reduction in the resistance of the thermistor 118A and an eventual decrease in the potential applied to the resistance heater 120A to reduce the temperature within the enclosure 112.

To adjust the heat flow control means 104, the potentiometer 124B is adjusted to different settings while the rate of flow of pure carrier fluid through the heat exchangers 108 and 114 and the heat of adsorption detector 10 is varied until a setting is found for which there is a minimum change in the difference between the temperature of the thermistors 29 and 46 (FIGS. 1 and 2) corresponding to the change in the rate of flow of the carrier. With this adjustment, the detection and identification of eluates by the heat of adsorption detector is unhindered by changes in the temperature of the thermistors 28 and 46 caused by changes in the rate of flow of fluid from the chromatograph column.

THEORY OF OPERATION

Figure 4:
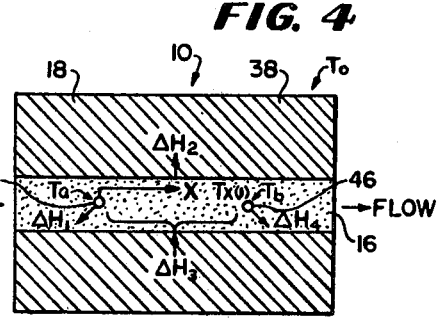
FIG. 4 is a longitudinal sectional view of a model of a portion of a heat of adsorption detector illustrating one explanation of the operation of the invention.

It is not completely understood why the means for controlling the flow of heat in a heat of adsorption detector reduces the sensitivity of the heat of adsorption detector to variations in the flow rate of the carrier through the heat of adsorption detector, but one explanation can be obtained from an analysis of the model shown in FIG. 4 of the heat of adsorption detector 10.

The model shown in FIG. 4 assumes that:

(1) thermistors 28 and 46 are located in a single cylindrical fluid passageway 16 within a single support body;

(2) the fluid passageway 16 is packed with a medium which has thermal conductivity properties and viscous friction properties which are constant throughout the length of the passageway, with fluid flow being from left to right in the passageway;

(3) the temperatures of the items listed in the first column of Table 1 are represented by the symbols in the second column;

(4) in Table 2, the differences between the temperatures listed in the first column are represented by the symbols in the second column;

(5) the heats listed in the first column of Table 3 are represented by the symbols listed in the second column; and (6) the symbol f represents the rate of flow of the carrier fluid and x is a point in the carrier fluid between the thermistors 28 and 46.

With the above assumptions, equations representing partial changes can be written from the model of FIG. 4 in the form $\overline{T}_n m = T_m - T_o$ to the heat flow n. For example, $\overline{T}1,a$ is $\overline{T}_a$ due to, and only to, heat flow $H_1$. Equations (1)–(4) are four sets of such equations.

By summing equations (1)–(4), equation (5) is written, describing the temperature difference $\bar{T}$ between the thermistors 28 and 46.

By differentiating $\bar{T}$ with respect to f, an expression shown in equation (6) is obtained that describes the rate of change of the temperature difference $\bar{T}$ between the thermistors 28 and 46 caused by variations in the rate of flow of of the carrier fluid.

TABLE 1

| items | symbol for temperature |
|---|---|
| fluid entering the passageway | $T_i$ |
| support body | $T_o$ |
| thermistor 28 and its vicinity | $T_a$ |
| thermistor 46 and its vicinity | $T_b$ |
| carrier fluid at point between thermistors 28 and 46 | $T_x$ |
| average temperature of carrier fluid between thermistors 28 and 46 | $T_{av}$ |

TABLE 2

| difference in temperatures: | symbol |
|---|---|
| $T_a - T_o$ | $\bar{T}_a$ |
| $T_x - T_o$ | $\bar{T}_x$ |
| $T_b - T_o$ | $\bar{T}_b$ |
| $T_{av} - T_o$ | $\bar{T}_{av}$ |
| $T_b - T_a$ | $\bar{T}$ |
| $T_i - T_o$ | $\bar{T}_i$ |

TABLE 3

| | |
|---|---|
| heat leaving the vicinity of the thermistor 28 due to electric heating of the thermistor 28 | $H_1$ |
| heat leaving the fluid carrier through the support body as the fluid carrier flows between thermistor 28 and thermistor 46 | $H_2$ |
| heat added to the fluid carrier by viscous friction while flowing between the thermistor 28 and the thermistor 46 | $H_3$ |
| heat leaving the vicinity of the thermistor 46 due to electric heating of the thermistor 46 | $H_4$ |

(1) for $H_1$: $\bar{T}_{1,a} = \bar{T}_{1,b} = \dfrac{H_1}{k_1 f}$ (2) for $H_2$: $\bar{T}_{2,a} = \bar{T}_{2,b} = \dfrac{T_{av}}{k_2 f}$ (3) for $H_3$: $\bar{T}_{3,b} - \bar{T}_{3,a} = k_3 f$ (4) for $H_4$: $\bar{T}_{4,a} = 0;\ \bar{T}_{4,b} = \dfrac{H_4}{k_1 f}$ (5) $\bar{T} = \bar{T}_b - \bar{T}_a = k_3 f + \dfrac{H_4}{k_1 f} - \dfrac{T_{av}}{k_2 f}$ (6) $d\bar{T}/df = k_3 - \dfrac{H_4}{k_1 f^2} + \dfrac{\bar{T}_{av} - f\, d\bar{T}_{av}/df}{k_2 f^2}$ where $k_1$ is a constant relating flow to temperature rise, primarily related to the heat capacity of the carrier fluid; $k_2$ is analagous to $k_1$; and $k_3$ is a coefficient related to viscous friction of the fluid in the stationary medium Equation (6) indicates the reasons that enable the heat flow control means 15, 62, and 104 to decrease the flow-rate-related error in the temperature readings of the heat of adsorption detector.

In equation (6), one of the flow-dependent terms is positive and one is negative. Moreover, one of the terms includes the factor $\bar{T}_{av} - f\, d\bar{T}_{av}/df$ and the sign of this factor is changeable. The flow rate dependent terms of the equation are adjusted by the heat control means 15, 62, and 104 to vary by approximately the same amounts in opposite directions as the rate of flow of the carrier fluid changes so as to reduce the flow-rate-related temperature error in the readings.

The term $f\, d\bar{T}_{av}/df$ in the above factor is generally insignificant for two reasons, which are: (1) the average temperature difference of a volume of fluid inherently changes more slowly than the temperature at a point in the volume so that $d\bar{T}_{av}/df$ will be small for larger changes in the temperature at specific points in the heat of adsorption detector; and (2) when properly adjusted, the heat of adsorption detector 10 is operated at points of minimum $d\bar{T}/df$ as shown in FIGS. 7 and 8 and described hereinafter and these are inherently close to points of minimum $d\bar{T}_{av}/df$.

Moreover, experience shows that the embodiments described in this case behave as if $f\, d\bar{T}_{av}/df$ were smaller than $\bar{T}_{av}$ or has the opposite sign from $\bar{T}_{av}$. Logically one would expect the sign of $f\, d\bar{T}_{av}/df$ to be opposite to that of $\bar{T}_{av}$, so that $-\, f\, d\bar{T}_{av}/df$ will have the same sign as $+\bar{T}_{av}$, thereby making these two terms additive and mutually effective. This is because $\bar{T}_{av}$ due to $H_1$ decreases as flow increases thus tending to make $f\, d\bar{T}_{av}/df$ negative and therefore $-\, f\, d\bar{T}_{av}/df$ positive.

Each of the three heat flow control means 15, 62, and 104 is an example of a different manner of controlling the flow of heat in the heat of adsorption detector 10 to cause the carrier flow-rate-dependent terms of the equation (6) to vary in opposite directions by approximately the same amounts as the flow rate of the carrier changes, or stated another way, is an example of a different manner of balancing the flow-rate-dependent terms of the equation.

Firstly, in the embodiment of FIG. 1, the flow-rate-dependent terms of equation (6) are balanced by changing the term containing $\bar{T}_{av}$, which is accomplished by changing the amount of heat imparted to the walls by the heat control means 15 and thereby changing the temperature $T_o$ of the walls of the heat of adsorption detector 10, $\bar{T}_{av}$ being the difference between $\bar{T}_o$ and the fluid temperature $T_{av}$.

Secondly, in the embodiment of FIG. 2, the flow-rate-dependent terms of equation (6) are balanced by changing the two flow related terms in opposite directions, which is accomplished by adjusting the potentiometer 94 of the heat control means 62 to: (1) change in a first direction the amount of heat $H_1$ released by the upstream thermistor 28 and thereby change $T_{av}$ and the term of equation (6) containing $\bar{T}_{av}$ in a first direction; and (2) change the amount of heat $H_4$ released by the downstream thermistor 46 in a second direction and thereby change the term of equation (6) containing $H_4$ in the second direction.

Thirdly, in the embodiment of FIG. 3, the flow-rate-dependent terms of equation (6) are balanced by changing $\bar{T}_{av}$, which is accomplished by adjusting the heat control means 104 to change the inlet termperature $T_i$ of the fluid entering the passageway 16, a change that can cause $\bar{T}_{av}$ to become either positive or negative by changing $T_i$ to a value above or below $T_o$.

FIGS. 5–8 provide another illustration of the manner in which the heat flow control means 15, 62, and 104 reduce the flow-rate-dependent temperature error of the heat of adsorption detector 10.

In FIG. 5, there is shown a graph 130 having ordinates of spurious $\overline{T}$ of error in the measured temperature difference between the reference thermistor 28 and the measuring thermistor 46 and abscissae of flow rate of the carrier fluid in the central fluid passageway 16. In the graph 130, a curve 132 of the relationship between the spurious $\overline{T}$ and the flow rate of the carrier fluid has portion 134 of rapidly increasing $\overline{T}$ with increasing flow rate which portion 134 occurs at relatively low flow rates, a portion 136 of maximum $\overline{T}$ which starts at the end of the portion 134 of rapidly increasing $\overline{T}$, a portion 138 of rapidly decreasing $\overline{T}$ with increasing flow rate, at flow rates higher than those at which the maximum $\overline{T}$ occur.

In FIG. 6, there is shown another graph 142 having ordinates of spurious $\overline{T}$ and abscissae of flow rate with three curves, showing the relationship between three of the causes of the variations of the spurious $\overline{T}$ of the heat of adsorption detector 10 with respect to the flow rate illustrated by curve 132 in FIG. 5 which three curves are: (1) curve 144 showing the relationship between spurious $\overline{T}$ caused by loss of heat through the walls of the heat of adsorption detector 10, which is considered a negative spurious $\overline{T}$ since it causes the measuring thermistor 46 to be cooler; (2) curve 146 showing the relationship between the spurious $\overline{T}$ caused by the release of heat from the second thermistor, which is a positive spurious $\overline{T}$ since it causes the measuring thermistor 46 to be warmer than the reference thermistor 28; and (3) curve 148 showing the relationship between the spurious $\overline{T}$ caused by viscous friction, which is a positive $\overline{T}$ since it causes the measuring thermistor 46 to be warmer than the reference thermistor 28.

The portions 134, 136, 138 and 140 of the curve 132 in FIG. 1 can be understood from the curves 144, 146 and 148 of the graph 142.

Firstly, the rapidly increasing $\overline{T}$ portion with increasing f 134 (FIG. 5) of the curve 132 is caused by a more rapid decrease in the heat lost to the walls as the flow rate increases as shown by curve 144 (FIG. 6) than the decrease in the temperature rise due to heat released by the second thermistor as shown by the curve 146 (FIG. 6). The rapid increase in the heat lost to the walls at lower flow rates as the flow rate decreases has two causes, which are: (1) the carrier fluid is between the reference thermistor 28 and the measuring thermistor 46 for a longer period of time permitting a greater transfer of heat from the carrier fluid through the walls; and (2) the slow rate of flow of the carrier fluid increases the temperature rise of the carrier fluid due to the increased time available for the transfer of heat from the reference thermistor 28 to each unit volume of the carrier fluid, with this increase in temperature causing more heat to be lost.

The portion 136 of the curve 132 occurs when the negative spurious $\overline{T}$ caused by heat loss through the walls and the positive spurious $\overline{T}$ caused by the heat released by the measuring thermistor 46 decrease at the same rate as shown by curves 144 and 146. This portion is of special interest because the total $\overline{T}$ is relatively constant with varying flow rates which cause flow-rate-dependent errors to be a minimum.

The portion 138 of rapidly decreasing $\overline{T}$ with increasing flow rates of the curve 132 occurs at flow rates for which the positive spurious $\overline{T}$ from the heating of the measuring thermistor 46 decreases at a faster rate than the negative spurious $\overline{T}$ from the heat lost to the walls. This occurs because the flow rate is sufficiently large to cool both thermistors without causing a large increase in the average temperature of the carrier fluid between the reference thermistor 28 and the measuring thermistor 46 and because the carrier fluid moves between the two thermistors faster so that it does not lose as much heat through the walls of the heat of adsorption detector.

The portion 140 (FIG. 5) of curve 132 for slowly decreasing spurious $\overline{T}$ with increasing flow rate occurs because the slowly increasing spurious $\overline{T}$ caused by viscous friction shown by curve 148 (FIG. 6) becomes sufficiently large to compensate partly for the decrease in the difference between the spurious $\overline{T}$ from heat loss through the walls and the spurious $\overline{T}$ from heat released by the temperature measuring thermistor 46.

The heat-flow control means 15, 62, and 104 have the effect of moving or broadening the portion 136 of the curve 132 to cover a wider range of flow rates. Without the heat-flow control means the heat of adsorption detctor 10 is unlikely to operate in the portion 136 of curve 132.

In FIGS. 7 and 8 there are shown graphs 150 and 152 respectively of experimental results from testing the embodiments of the heat of adsorption detectors shown in FIGS. 3 and 2, respectively, each having ordinates of the rate change, $d\overline{T}/df$, of spurious $\overline{T}$ magnitude and phase with respect to a flow rate f, with the graph 150 having abscissae $\overline{T}_i$ of the difference between the temperature $T_i$ of the carrier fluid entering the central fluid passageway and the temperature $T_o$ of the walls of the heat of adsorption detector 10 and with the graph 152 having abscissae of units of power added to the reference thermistor 28. In making the measurements for these graphs, an average flow rate of 50 ml/hr with a 5 percent variation in the flow rate at 0.5 cpm was used to approximate df for the graph 150 and an average flow rate of 50 ml/hr with a 6 percent variation in the flow rate at 0.5 cpm was used to approximate df for the graph 152.

These graphs provide a further illustration of the operation of the heat-flow control means when considered with equation (6) and the graphs 130 and 142 of FIGS. 5 and 6.

The graph 150 of FIG. 7 includes a curve 154 indicating the relationship of the magnitude of variation in the spurious $d\overline{T}/df$ and a curve 156 indicating the relationship of the phase of the spurious $d\overline{T}/df$ with respect to variations in the input temperature $\overline{T}_i$ of the carrier fluid.

The curve 154 includes a portion 158 of declining spurious $d\overline{T}/df$ and a portion 160 of increasing spurious $d\overline{T}/df$, with the portion 158 of declining $d\overline{T}/df$ declining from a negative input temperature to a slightly positive temperature indicated at 162 and with the portion 160 of increasing $d\overline{T}/df$ increasing from the temperature at 162 to a positive temperature, the slightly positive temperature at 162 being the temperature of the input carrier fluid that provides the least variation in $\overline{T}$ with changes in flow rate.

The curve 156 includes a portion 164 of negative phase for $d\overline{T}/df$ and a portion 166 of positive phase with the portion 164 being shown along the abscissae between a negative value of $\overline{T}_i$ and O indicating that increasing flow rates of carrier fluid causes a decrease in $\overline{T}$, resulting in a negative phase for $d\overline{T}/df$.

From an examination of the curves 154 and 156, it can be understood that there is an approximate reduction in the flow-rate-dependent temperature error of the heat of adsorption detector 10 in the embodiment of FIG. 3 of four to one with a 90° phase angle when the inlet temperature is slightly positive as indicated at 162, compared to when $\overline{Ti} = 0$.

Firstly, the reason for the reduction in the flow-rate-dependent temperature error can be understood from an examination of equation (6) in the light of the curve 154 and 156. Increasing the temperature of the carrier fluid entering the heat of adsorption detector 10 increases $\overline{T}_{av}$ in a positive direction so that the term of equation (6) that includes $T_{av}$ balances the other flow-rate-dependent term of the equation, resulting in a reduction in the flow-rate-dependent temperature error. The inlet temperature at point 162 in the graph 150 (FIG. 7) is the temperature that balances equation (6).

Secondly, the reason for the reduction in the flow-rate-dependent temperature error can be understood from a consideration of the curve 132 (FIG. 5) in the light of the curves 154 and 156 (FIG. 7). The heat of adsorption detector 10 normally operates in the region 138 of curve 132 (FIG. 5) of rapidly decreasing spurious T with respect to flow rate f. When the temperature of $T_i$ of incoming carrier fluid is increased to the point 162 of graph 150, the region 136 of curve 132 is shifted to the operating rate of flow of the heat of adsorption detector 10. This occurs because increasing the flow rate f causes the higher heat level from the warmer inlet to flow down to the second thermistor with less reduction in temperature from the heat loss to the walls. This effect is shown by the curve 154 (FIG. 7) in which an inlet temperature equal to or below that of the body temperature $T_o$ of the heat of adsorption detector results in a decreasing $d\overline{T}/df$ as shown by the portion 158 of the curve 154 and an inlet temperature above that of the body temperature $T_o$ of the heat of adsorption detector results in an increasing dT/df as shown by the portion 160 of the curve 154.

The graph 152 of FIG. 8 includes a curve 168 and a curve 170, with the curve 168 indicating the magnitude of variation in the spurious $d\overline{T}/df$ with variations in the power added to thermistor 28 to increase the heat $H_1$ emitted by this thermistor and with the curve 170 indicating the phase of the spurious $d\overline{T}/df$ with respect to variations in the power added to thermistor 28 to increase the heat $H_1$ emitted by this thermistor.

The curve 168 includes three portions, which are: (1) a portion 172 of declining $d\overline{T}/df$ with increasing power added to the thermistor 28, occurring at low additions; (2) a portion 174 of increasing $d\overline{T}/df$ with increasing power added to the thermistor 28, occurring at high power additions; and (3) a portion 176 of minimum $d\overline{T}/df$ occurring at amounts of power added to the thermistor 28 between the amounts added for portion 172 and portion 174. The curve 170 generally indicates an increasing phase angle between the variations in flow rate and the spurious $d\overline{T}/df$.

From an examination of the curve 168, it can be udnerstood that there is an approximate reduction in the flow-rate-dependent temperature error of the heat of adsorption detector 10 in the embodiment of FIG. 2 of three and one-quarter to one when sufficient power is added to thermistor 28 to operate in the portion 176 of curve 168.

In FIG. 9, there is shown a block diagram of an interferometric refractometer 180 having a polarized light source 182, a beam splitter 184, a quarter wave plate 186, a beam combiner and phase comparator 188, a recorder 190, and a fluid-characteristic measuring station 192.

The light source 182, beam splitter 184 and quarter wave plate 186 are arranged with respect to each other so that light from the light source 182 is split by the beam splitter 184 into two beams having the same phase, one of which passes through the quarter wave plate 186 before being applied to the fluid-characteristic measuring station 192 and the other of which is applied directly to the fluid-characteristic measuring station 192 through an equal optical-length path. The two beams are transmitted through different flow streams within the fluid-characteristic measuring station 192. The beam combiner and phase comparator is positioned with respect to the fluid-characteristic measuring station 192 to receive both beams of light after the two beams of light have passed through the fluid streams and is electrically connected to the recorder 190 to record a signal which results from the combining and phase comparison of the beams of light.

This refractometer is described more completely in "A Laser Interferometric differential Refractometer For Detection of Chromatographic Effluent and Measurement of Volume Elasticity of Liquids" by H. F. Hazebroek, Journal of Physics E: Scientific Instruments, 1972, Vol. 5, pps. 180-185. The beam combiner and phase comparator 188 as described in that publication, develops a signal representing the refractive index of one of the two fluids in the measuring station 192 and records that signal.

The fluid-characteristic measuring station 192, in the preferred embodiment includes two flow cells 194 and 196, together with apparatus to cause liquid to flow through the flow cells while beams of light are passed through them and certain temperature control apparatus.

To cause fluid to pass through the flow cell 194, the fluid-characteristic measuring station 192 includes a source of effluent 198, connected by tubing 200 to the inlet port of the flow cell 194, with an exit port being connected by tubing 202 to a drain for the fluid (not shown). In the center of the flow cell, the fluid flows through a path aligned with the longitudinal axis of the flow cell having windows on each side of it so that the first beam of light which passes through the quarter wave plate 196 passes through a substantial length of the fluid before being transmitted from the fluid-characteristic measuring station to the beam combiner and phase comparator.

To cause fluid to pass through the flow cell 196, the fluid-characteristic measuring station 192 includes a reference solvent source 204, connected to the inlet port of the flow cell 196 through tubing 206, with an exit port of the flow cell 196 being connected by tubing 208 to a drain for the fluid in a manner similar to the flow cell 194. The flow cell 196 is constructed in a manner similar to that of 194 so that it receives the second beam of light from the beam splitter 184 and transmits it through a length of the reference solvent before transmitting it to the beam combiner and phase comparator 188.

To control the temperature within portions of the fluid-characteristic measuring station 192 in such a way as to reduce flow-rate related errors in one embodiment, the fluid-characteristic measuring station includes a first heat exchanger 210 and a second heat exchanger 212 with the flow cells 194 and 196 being within the first heat exchanger and the inlet tubing 200 and 206 immediately adjacent to the inlet ports of the flow cells 194 and 196 being also within the second heat exchanger 212. These heat exchangers may be similar to the heat exchangers 106 and 112 in the embodiment of FIG. 3 and are controlled in temperature with respect to each other by a temperature control circuit similar to the circuit shown in FIG. 3.

The first and second heat exchangers, as shown in FIG. 9 include a temperature control unit 214, a temperature sensing device 216 within the first exchanger 210, a heater 218 within the first heat exchanger 210, a temperature sensing device 220 within the second heat exchanger 212 and a heater 222 within the second heat exchanger 212. The heat exchangers 210 and 212 control the temperature of the fluid in the inlet tubing to the flow cells 194 and 196 with respect to the temperature of the body of the flow cells 194 and 196 to reduce the flow-rate-related temperature deviations of the fluid within the flow cells while characteristics of the fluid are being measured in the manner explained in connection with FIG. 3.

In another embodiment, the fluid-characteristic measuring station 192 includes heater coils 224 and 228 and temperature control equipment which may be used either in cooperation with the heat exchangers 210 and 212 or without them to reduce flow-rate related errors by heating the walls of the flow cells 194 and 196. The amount of heat generated by each heating coil is independently adjustable so that the walls of each flow cell can be adjusted in temperature with respect to the other flow cell.

To adjust the temperature of the wall of flow cell 194, the heating coil 224 is wound around the flow cell and electrically connected to a temperature control unit 226 in a manner similar to the arrangement for heating the walls of heat of interaction detector shown in FIG. 1. Similarly, to adjust the temperature of the wall of the flow cell 196, heating coil 228 is wound around it and electically connected to a temperature control unit 230. The temperature control units 226 and 230 are adjustable and transmit different amounts of electrical current through their respective heating coils, thus controlling the temperature of the walls of the flow cells.

To control the temperature of the fluid flowing through the flow cell 194 in a third embodiment, the fluid-characteristic measuring station 192 includes temperature control units 232 and 236 and heaters 234 and 238 with the temperature control unit 232 being connected to a heater 234 within the flow path of fluid flowing through the flow cell 194 such as within the tubing 200 adjacent to the inlet port of the flow cell 194 and with the temperature control unit 236 being electrically connected to a heater 238 within the tubing 206 adjacent to the inlet port of the flow cell 196. Of course, the heaters may be adjacent to the tubing to heat the tubing or may be outside the tubing but in contact with a heat conductor within or adjacent to the tubing so as to be in thermal contact with the fluid.

While two heat exchangers 210 and 212 are shown in FIG. 9, with heat exchanger 210 enclosing the flow cells 194 and 196 and heat exchanger 212 enclosing the inlet tubing 200 and 206, more or fewer heat exchangers may be employed in a refractometer. For example, instead of one heat exchanger for both flow cells, a different heat exchanger may be provided for each flow cell. Similarly, a different flow cell may be provided for the inlet tubing to each flow cell. Moreover, some beneficial results are obtained from controlling only the temperature of either the flow cells, with the inlet tubing being at ambient temperature, or of the inlet tubing, with the flow cells being at ambient temperature.

In some instruments more flow cells or fewer flow cells are required than in the embodiments described herein or a cell in which a reference fluid is held stationary in its passageway may be substituted for the flow cell through which the reference fluid flows. In other instruments other types of housings are required than in the refractometer of FIG. 9. Such instruments may accordingly require more or fewer heat exchangers to provide the required flexibility of control. Similarly, it may only be necessary to control a single housing or inlet to the housing with a single heat exchanger for some applications.

Before operating the refractometer, to determine the refractive index of materials in a flow stream, two known identical fluids are pumped through the flow cells while the refractometer is operated and the temperature devices are adjusted as the flow rates are varied for the fluids until there is a minimum indication of the difference in the refractive index between the two materials with the fluctuations in the flow rate. Once the proper temperatures are set, the refractometer is operated to determine the refractive index of materials and thus identify the materials in one of the flow streams.

In one embodiment, the refractometer is adjusted for minimum error from variations in flow rate of the fluids using the heat exchangers 212 and 210 and not using the heating coils 224 and 228 nor the transducers 234 and 238 for temperature adjustments. To adjust the refractometer for minimum error before using it in this embodiment, solvents are first applied from the effluent source 198 and the reference solvent source 204 through their respective conduits 200 and 206 and through the flow cells 194 and 196. Both solvents are identical in this case so that an error-free comparison of the refractive index would indicate no differences.

While these identical fluids are being pumped through the flow cells 194 and 196, the light source 182 transmits a polarized laser beam through the beam splitter 184 which splits the beam into two parallel beams. A first of the beams is transmitted through the quarter wave plate 186 which creates a circular polarization in it and then transmits it through the fluid in the first flow cell 194 to the beam combiner and phase comparator 188. The second beam from the beam splitter 184 is applied through an optical-length path equal to the optical-length of the first path directly through the fluid in the flow cell 196 and then to the beam combiner and phase comparator 188.

The beams are combined in the beam combiner to obtain fringes from phase differences caused by differences in the refractive indices of the materials in the flow cells and these fringes are sensed and recorded by the recorder 190 to indicate the phase difference between the two beams of light caused by differences in the refractive indices of these two flow cells.

While the refractive indices are being measured with identical fluids flowing through both flow cells, the rates of flow of the fluids are varied. While the rates of flow are varied, the heat exchangers 210 and 212 are adjusted in temperature with respect to each other and with respect to an absolute temperature by the temperature control unit 214. This adjustment causes a difference in the changes in temperature between the identical fluid streams passing through the inlet conduits from the effluent source 198 and reference solvent source 204 and the temperature of the walls of the flow cells 196 and 194, with the temperature of the fluids which are controlled by the heat exchanger 212 generally being higher than the temperature of the flow cells controlled by the heat exchanger 210. This mode of operation is similar to the operation described in connection with FIG. 3.

As the flow rates are varied and the temperatures of the heat exchangers are adjusted with respect to each other, the difference in refractive index caused by variations in the flow rates is observed on the recorder 190. The temperature is adjusted until the differences in refractive index as indicated on the recorder 190 are at a minimum and then the settings are maintained by the temperature control unit 214.

Once the proper temperatures between the heat exchangers 210 and 212 have been located and set, the effluent, which is being investigated replaces the pure solvent from the effluent source 198 and the refractometer is operated. During its operation, the refractive index of the effluent is obtained by a comparison of the known refractive index of the reference solvent which comparison is indicated by the recorder 190 with a minimum of error due to fluctuations in the flow rate of the fluids.

It is not completely understood why fluctuations should occur in the refractive index due to variations in the flow rate but it is believed that these are due to temperature effects. Changes in temperature caused by changes in flow rate affect the refractive index of many materials and since changes in flow rates occur between the effluent source and reference source the comparison of refractive index between the two materials are effected.

It is believed that the proper differance of the temperature between the inlet fluid and the housing causes the flow-rate related temperature effects to reach a minimum when two such fluids are compared in a manner similar to that illustrated in FIG. 7 for the heat of absorption detector although the equations for heat loss from the heat of absorption detector would not be identical to those for the refractometer. Nevertheless, by analogy, the same type of curve is expected by balancing the temperature errors caused by variations of flow rate which increase with an increase in flow rate against those that decrease with an increase in flow rate and vice-versa by adjusting the heat flow paths within the flow cells.

The heating coils 224 and 228 reduce flow-rate-dependent errors in measurements of characteristics of fluids in a manner analogous to the heat exchangers 210 and 212 and analogous to the heating coil 15 in the embodiment of FIG. 1 of the heat of absorption detector. They may be used either separately from or in conjunction with the heat exchangers 210 and 212 to provide individual adjustment of the temperature of the bulk of the flow cells 194 and 196, thus adjusting the temperature of the flow cells with respect to each other as well as the temperature of the flow cells with respect to the fluid entering the flow cell. When used in conjunction with the heat exchangers 210 and 212, they provide a differential between the two flow cells while the heat exchangers 210 and 212 aid in controlling the temperature difference between the fluid entering the flow cells and the flow cells.

To adjust the temperature of the flow cells, the amount of current passing through the heating coils 224 and 228 is adjusted by means of the temperature control units 226 and 230 respectively, thus adjusting the heat generating in the coils and the temperature at which the flow cells are maintained by the heating coils. While temperature adjustments are made, the same identical fluids flow through each flow cell and changes in the index of refraction indicated by the recorder 190 are observed. The settings are experimentally determined in this manner while the flow rates of the fluid fluctuate until differences between the refractive indices of the two fluids with fluctuations in flow rates are at a minimum. The refractometer is then operated to determine the refractive index of an unknown substance from the effluent source 198.

A third type of adjustment shown in FIG. 9 utilizes the transducers 234 and 238 to control the temperature of fluid entering the flow cells. These transducers are heaters immersed in the fluid or formed as heating elements immediately around the tube adjacent to the flow path to cause heat to be conducted into the flow path. The amount of heat given off by the transducers 234 and 238 is adjusted by the temperature control units 232 and 236 respectively, which may include potentiometers or the like for adjusting the flow of current applied to the heating elements.

The transducers 234 and 238 are adjusted while the identical solvents are pumped through the flow cells with a fluctuating flow rate until the refractive index difference between the two fluids are indicated on the recorder 190 is a minimum. Once this adjustment is reached, an unknown effluent may have its index of refraction determined by pumping it through the effluent source 198 and comparing it to the index or refraction from the solvent in the reference solvent source 204 as indicated by the recorder 190. This individually adjustable temperature technique can be used in conjunction with the heat exchangers 210 and 212 in the same manner as the individually adjustable heating coils 224 and 228 may be used.

The individually adjustable heaters for individual flow cells shown in FIG. 9, which are heating coils 224 and 228 and transducers 234 and 238 may be used to control the temperature of one flow cell with respect to another or to control one portion of one flow cell. For example, if the reference solvent is held captive and stationary in flow cell 196, it is only necessary to reduce errors in measuring flow cell 194 and this can be accomplished by controlling one transducer to heat the inlet fluid and/or one heating coil to control the flow cell 194. Similarly, the flow-rate related errors may be reduced under some circumstances by controlling only the temperature of the housing or the temperature of the fluid.

While instruments have been described to identify unknown substances carried by a fluid by their heat of adsorption or refractive index, other types of devices may be built in accordance with the invention or inventions which operate in other modes to utilize the invention of this application or the invention of copending application Ser. No. 251,712 referred to hereinabove. It is only necessary that: (1) a characteristic of a fluid or fluids is to be detected; (2) the detection of the characteristic is affected by temperature changes in the fluid; (3) the temperature changes are created by flow rate changes of a fluid with respect to its housing and/or with respect to another fluid in another flow stream; and (4) some of the components of the temperature changes increase and others decrease with the same direction of change of the rate of flow.

From the above description, it can be understood that the instrument of this invention has the advantages over prior art instruments of: (1) providing consistent and reproducible reductions in flow-rate-dependent errors in measuring a characteristic of a fluid; (2) being less sensitive to fluctuations in the ambient temperature; (3) being easily adjusted for minimum flow-rate-dependent errors when required by different conditions of measurements; and (4) being adaptable to a wide range of instruments for measuring the characteristics of fluid rather than being only usable with heat of interaction detectors.

Although preferred embodiments of the invention have been described with some particularity, many modifications and variations in the preferred embodiments may be made without deviating from the invention. Accordingly, it is to be understood that, within the scope of the appended claims, the invention may be practiced otherwise than as specifically described.

What is claimed is:

1. Apparatus for reducing a flow-rate-dependent errors in an instrument for measuring a characteristic of fluids comprising:

control means for controlling the difference between the temperature at a first location within the instrument and the temperature at a second location within the instrument;

said control means includes a balancing means for adjusting the heat flow in one of said locations to at least partly balance a flow-rate-dependent error that decreases as the flow rate changes in a predetermined direction against a flow-rate-dependent error that increases as the flow rate changes in said predetermined direction.

2. Apparatus according to claim 1 in which said control means includes means for controlling the temperature of the fluid entering the instrument with respect to the body of the instrument.

3. Apparatus according to claim 2 in which said instrument further comprises:

first inlet means for receiving a first fluid;

second inlet means for receiving a second fluid;

outlet means for permitting the first and the second fluids to leave said instrument;

first flow path means between the first inlet means and the outlet means for permitting the flow of the first fluid between the first inlet means and the outlet means;

second flow path means between the second inlet means and the outlet means for permitting the flow of the second fluid from the second inlet means to the outlet means;

first flow-rate-related means for causing flow-rate-dependent error increases within the instrument as the flow rate of at least one of the fluids changes in a predetermined direction and second flow-rate-related means for causing flow-rate-dependent error decreases within the instrument as the rate of flow of the fluid changes in the predetermined direction;

means for generating a first signal related to the characteristic of the first fluid;

means for generating a second signal related to the characteristic of the second fluid;

means for generating a third signal related to a comparison between the first and second signals;

means for varying the rate of flow of at least one of said first and second fluids;

means for balancing said first flow-rate-related means against said second flow-rate-related means, whereby said error from said flow-rate-dependent variations is reduced; means for sending the fluid the characteristic of which is to be measured through one of said first and second flow path means; and means for measuring said characteristic.

4. Apparatus according to claim 3 in which:

said means for varying the rate of flow of at least one of said first and second fluids includes means for varying the rate of flow of one of said fluids through one of said flow path means;

said means for measuring said characteristic includes means for comparing the same characteristic of the first fluid and the second fluids.

5. Apparatus according to claim 4 in which:

said first and second flow path means including wall portions defining first and second passageways;

said means for controlling the temperature of the fluid entering the instrument includes means for adjusting at least the temperature of the fluid in one of said first and second passageways with respect to the temperature of the walls of the passageway through which said fluid flows while the rate of flow of at least one of said first and second fluids is varied and the rate of change of the flow-rate-dependent error is detected until the flow-rate-dependent error is relatively low.

6. Apparatus according to claim 2 in which said instrument comprises:

an inlet for fluids;

a body defining a flow path for said fluids; and an outlet;

said control means including a means for controlling the temperature of at least one fluid entering said inlet means with respect to said body of said instrument.

7. Apparatus according to claim 2 in which said means for controlling the temperature of the fluid entering the instrument includes means for adjusting at least the temperature of one fluid flowing in one fluid path into the instrument with respect to the temperature of the body of the passageway of said instrument through which said stream flows while the rate of flow of at least one of said fluid is varied and the rate of change of the flow-rate-dependent error is detected until the flow-rate-dependent error is relatively low.

8. Apparatus according to claim 1 in which said control means includes means for controlling the heat emitted by a heating device in thermal contact with the flow path of said fluid.

9. Apparatus according to claim 8 in which said balancing means includes:

at least one flow path means; and means for varying the rate of flow of fluid through said flow path means.

10. Apparatus according to claim 1 in which said instrument includes at least one inlet for receiving a fluid, at least one outlet for draining said fluid and a body defining a flow path means for said fluid; said control means including an adjustable means for applying heat to the body of said instrument.

11. Apparatus according to claim 10 further including;

means for varying the rate of flow of at least one fluid through said flow path mean; and means for measuring a characteristic of the fluid in the flow path.

12. Apparatus according to claim 11 in which said control means includes means for adjusting the temperature difference between a fluid entering the instrument and the temperature of the body of the passageway of said instrument through which said fluid flows while the rate of flow of said fluid is varied and the rate of change of the flow-rate-dependent error is detected until the flow-rate-dependent error is relatively low.

13. Apparatus according to claim 1 in which said balancing means includes adjustable means for adjusting the flow of heat through the instrument while the instrument is operated until the flow-rate-dependent error is at a relatively low level.

14. An instrument according to claim 1 in which said balancing means for adjusting the heat flow in one of said locations includes means for applying heat to said one of said locations for the purpose of at least partly balancing a flow-rate-dependent error that decreases as the flow rate changes in a predetermined direction against a flow-rate-dependent error that decreases as the flow rate changes in said predetermined direction.

15. Apparatus according to claim 14 further including:

first and second flow path means for permitting the flow of first and second fluids through said instrument;

means for varying the rate of flow of at least one of said first and second fluids through a corresponding one of said flow path means; and means for comparing the same characteristic of the first fluid and the second fluid.

16. A method according to claim 15 further including means for controlling the temperature difference between the fluid entering the first and second flow path means and said first and second flow path means through which the fluid flows while the rate of flow of the fluid is varied and the rate of change of the flow-rate-dependent error is detected until the flow-rate-dependent error is relatively low.

17. An instrument comprising:

a first enclosure;

first negative-feedback means for controlling the temperature of said first enclosure;

means for measuring a characteristic of fluids;

said means for measuring being located in said first enclosure;

a second enclosure;

second negative-feedback means for controlling the temperature of said second enclosure;

means for adjusting the temperature difference between the said first and second enclosures;

a heat exchanger;

said heat exchanger being located in said second enclosure;

fluid inlet means connected to one side of said heat exchanger; and fluid transfer means for coupling the other side of said heat exchanger to the means for measuring.

18. Apparatus according to claim 17 in which said means for measuring includes means for comparing the refractive index of two fluids.

* * * * *

UNITED STATES PATENT AND TRADEMARK OFFICE
CERTIFICATE OF CORRECTION

PATENT NO. : 4,140,396

DATED : February 20, 1979

INVENTOR(S) : Robert W. Allington

It is certified that error appears in the above-identified patent and that said Letters Patent are hereby corrected as shown below:

Column 1, line 32, change the word "absorb" to "adsorb".

Column 1, line 40 and 41, change the word "absorption" to "adsorption".

Column 3, line 46, change the word "excahngers" to "exchangers".

Column 4, line 25 and 26, change the word "repreducible" to "reproducible".

Column 5, line 3, change the word "longitudianl" to "longitudinal".

Column 7, line 14, change the word "compounts" to "compounds".

Column 9, line 25, change the word "absorption" to "adsorption".

Column 10, line 62, change the word "and" to "end"

Column 11, line 68, change "transformer 82" to "transformer 84".

Column 12, line 18, change the word "absorption" to "adsorption".

Column 13, line 44, change the word "to" to "of".

Column 14, line 26, change "29" to "28".

Column 15, line 8, change "flow of of" to "flow f of".

UNITED STATES PATENT AND TRADEMARK OFFICE
CERTIFICATE OF CORRECTION

PATENT NO. : 4,140,396

DATED : February 20, 1979

INVENTOR(S) : Robert W. Allington

It is certified that error appears in the above-identified patent and that said Letters Patent are hereby corrected as shown below:

Column 15, line 65, change the word "absorption" to "adsorption".

Column 15, line 68, change "$T_{av}-fdT_{av}/df$" to "$\overline{T}_{av}-fd\overline{T}_{av}/df$".

Column 16, line 61, change the word "termperature" to "temperature".

Column 17, line 39, change the word "lost" to "loss".

Column 17, line 43, change the word "lost" to "loss".

Column 17, line 67, change the word "lost" to "loss".

Column 19, line 4, change "$\overline{T}i=0$" to "$\overline{T}_i=0$".

Column 19, line 22, change "$T$" to "$\overline{T}$".

Column 19, line 36, change "$dT/df$" to "$d\overline{T}/df$".

Column 20, line 22, change "differential" to "Differential".

Column 23, line 40 and 41, change the word "absorption" to "adsorption".

Column 23, line 42, change the word "absorption" to "adsorption".

Column 23, line 45, change the word "absorption" to "adsorption".

Column 24, line 29, change the word "are" to "as".

UNITED STATES PATENT AND TRADEMARK OFFICE
CERTIFICATE OF CORRECTION

PATENT NO. : 4,140,396
DATED : February 20, 1979
INVENTOR(S) : Robert W. Allington It is certified that error appears in the above—identified patent and that said Letters Patent are hereby corrected as shown below:

Column 24, line 33, change the word "or" to "of".

Column 25, line 29, after the semicolon, add the word "and".

Column 26, line 2, after the semicolon, add the word "and".

Column 26, line 15, after the semicolon, add the word "and".

Column 26, line 21, after the semicolon, add the word "and".

Column 26, line 35, after the semicolon, omit the word "and".

Column 26, line 36, after the semicolon, add the word "and".

Column 26, line 68, change the semicolon to a colon.

Column 27, line 2, change the word "mean" to "means".

Signed and Sealed this

*Fifteenth* Day of *January 1980*

[SEAL]

*Attest:*

SIDNEY A. DIAMOND

*Attesting Officer*     *Commissioner of Patents and Trademarks*